US007541041B2

(12) United States Patent
da Conceição Tavares Gomes et al.

(10) Patent No.: US 7,541,041 B2
(45) Date of Patent: Jun. 2, 2009

(54) VACCINE AGAINST DENTAL CARIES BASED ON VIRULENCE-ASSOCIATED IMMUNOMODULATORY EXTRACELLULAR PROTEINS PRODUCED BY THE CARIOGENIC BACTERIA STREPTOCOCCUS SOBRINUS AND STREPTOCOCCUS MUTANS

(75) Inventors: Maria Delfina da Conceição Tavares Gomes, Porto (PT); Paula Maria das Neves Ferreira da Silva, Maia (PT); Manuel João Rua Vilanova, Couto St. Tirso (PT); António José de Meneses Moreira da Fonseca, Coimbra (PT); António Manuel Silvério Cabrita, Coimbra (PT); António Manuel Pinto do Amaral Coutinho, Lisboa (PT)

(73) Assignee: UPIN - Universidade Do Porto Inovacao, Porto (PT)

( * ) Notice: Subject to any disclaimer, the term of this patent is extended or adjusted under 35 U.S.C. 154(b) by 550 days.

(21) Appl. No.: 10/913,723

(22) Filed: Aug. 6, 2004

(65) Prior Publication Data
US 2006/0029618 A1 Feb. 9, 2006

(51) Int. Cl.
*A61K 8/02* (2006.01)
*A61K 8/66* (2006.01)
*A61K 8/96* (2006.01)
*A61K 9/46* (2006.01)
*A61K 39/38* (2006.01)
*A61K 39/085* (2006.01)
*A61K 39/02* (2006.01)
*A61K 39/09* (2006.01)
*A61K 45/00* (2006.01)
*A61K 47/00* (2006.01)
*A61Q 11/00* (2006.01)

(52) U.S. Cl. ............... 424/237.1; 424/184.1; 424/401; 424/466; 424/50; 424/234.1; 424/244.1; 424/278.1

(58) Field of Classification Search ................... None
See application file for complete search history.

(56) References Cited

U.S. PATENT DOCUMENTS

2006/0029618 A1* 2/2006 da Conceicao Tavares Gomes et al. ................ 424/224.1
2007/0178054 A1* 8/2007 Srinivasa et al. ............ 424/50

FOREIGN PATENT DOCUMENTS

EP 524732 A2 * 1/1993

OTHER PUBLICATIONS

Dinis et al, J. Dent. Res., 2004, 83/4:354-358.*
Koga et al, Vaccine, 2002, 20:2027-2044.*
Tenovuo et al, Proceedings of Finnish Dental Society, Suomen Hammaslaakariseuran toimituksia, 1991, 87/4:449-461, abstract only.*
Mosci et al, Minerva stomatologica, May 1990, 39/5:413-429 abstract only.*
van Palenstein Helderman et al, J. Dental Research, Jan. 1996, 75/1:535-545, abstract only.*
Quivey et al, Oral Microbiology and Immunology, 2006, 233-252, abstract only.*
Caufield et al, Compendium of Continuing Education in Dentistry, May 2005, 26/5 Suppl. 1:10-16 abstract only.*
Hamada, Pure and Applied Chemistry, 2002, 74/7: 1293-1300.*
Hanada, Japanese J. Infectious Diseases, Feb. 2000, 53/1:1-5, abstract only.*
de Soet et al, Caries Research, 1991, 25/2:116-122 abstract only.*
Napimoga et al, J. Oral Sciences, 2005, 47/2:59-64.*
Munro et al, FEMS Microbiology Letters, 1995, 128:327-332.*
Bratthall, International Dental Journal, 1995, 45:245-254.*
Emilson, J. Dent. Res., Mar. 1994, 73/3:682-691.*
Schilling et al, Infection and Immunity, Jun. 1992, 60/1:284-295.*
Hamada et al, J. Dental Research, 1976, 55(Spec.):C65-C74.*
Kuykindoll et al, Infection and Immunity, Sep. 1996, 64/9:3652-3658.*
Tanzer et al, Infection and Immunity, Jul. 1974, 10/1:197-203.*
Harris et al, Infection and Immunity, Aug. 1992, 60/8:3175-3185.*
Jones, Medical Hypotheses, 2003, 60/2:171-174.*
Quivey et al, Advances in Microbial Physiology, 2000, 42:239-274.*
Ajdic et al, PNAS, Oct. 29, 2002, 99/22:14434-14439.*
Smith et al, Infection and Immunity, May 2005, 73/5:2797-2804.*
Russell et al, Caries Research, 2004, 38:230-235.*
Madureira et al, J. Immunology, 2007, 178:1379-1387.*
Jones et al, BBRC, 2007, 364:924-929.*
Wilkins et al, Applied and Environmental Microbiology, May 2002, 68/5:2382-2390.*
Dinis et al, J. Infectious Diseases, Jan. 1, 2009, 199/1:116-123.*
Arala-Chaves MP, Ribeiro A, Vilanova M, Porto MT, Santarém, MMG and Lima M. 1988. "Correlation between B cell mitogenicity and immunosuppressor effects of a protein released by porcine monocyte infected with African swine fever virus." *Am J Vet Res* 49:1955.

(Continued)

*Primary Examiner*—N. M Minnifield
(74) *Attorney, Agent, or Firm*—Brinks Hofer Gilson & Lione

(57) ABSTRACT

This invention is concerned with a vaccine against dental caries obtained from the supernatant over cultures of the cariogenic bacteria *Streptococcus sobrinus* and *S. mutans* that consists of extracellular proteins. These proteins provide the suppression of the immune response in the host through the early production of IL-10, an anti-inflammatory cytokine and are, for that reason, virulent factors to the microorganism enhancing bacterial load in the host. These proteins were designated as virulence-associated immunomodulatory extracellular proteins (VIP). Vaccination through the host immunization with active VIP in a submitogenis dose, inactivated VIP or enolase in a dose unable to induce immunosuppression, induces the immunoneutralization of the VIP immunobiological effects.

Vaccination can be used both as a preventive or therapeutic measure of dental caries as long as it is administered (intranasally, orally or subcutaneously) into mammals before or after bacterial infection, respectively.

20 Claims, 3 Drawing Sheets

OTHER PUBLICATIONS

Lima A, Bandeira A, Portnoi D, Ribeiro A, Arala-Chaves MP. 1992. "Protective effect of a T-cell-dependent, immunosuppressive, B-cell-mitogenic protein (F3' EP-Si or p90) produced by *Streptococcus intermedius.*" *Infect Immun* 60: 3571.

Ferreira P, Soares R, Ribeiro A, and Arala-Chaves M. 1988. "Correlation between specific immunosuppression and polyclonal B cell activation induced by a protein secreted by *Streptococcus mutans,*" *Scand J Immunol* 27 : 549.

Tavares D, Salvador A, Ferreira P, and Arala-Chaves M. 1993. "Immunological Activities of a *Candida albicans* Protein Which Plays an Important Role in the Survival of the Microorganism in the Host." *Infect Immun* 61: 1881.

Tavares D, Ferreira P, Vilanova M. Videira A and Arala-Chaves M. 1995. "Immunoprotection against systemic candidiasis in mice." *Int Immunol* 7:785.

Soares R, Ferreira P, Santarém MMG, Teixeira da Silva M, and Arala-Chaves, M. 1990. "Low T- and B-cell Reactivity is an Apparently Paradoxical Request for Murine Immunoprotection Against *Streptococcus mutans.*" *Scand. J. Immunol* 31:361.

Reina-San-Martin B, Degrave W, Rougeot C, Cosson A, Chamond N, Cordeiro-Da-Silva A, Arala-Chaves M, Coutinho A and Minoprio Paola. "A B-cell mitogen from a pathogenic trypanosome is a eukaryotic proline racemase." *Nature Medicine* 6: 890.

Loesche, WJ. 1996. "Role of *Streptococcus mutans* in Human Dental Decay." *Microbiol Rev* 50:353.

De Soet JJ, Van Leveren C. Lammens AJ, Pavicic MJA, Homburg Che, Cate JM and Graaff J. 1991. "Differences in Cariogenicity between Fresh Isolates of *Streptococcus sobrinus* and *Streptococcus mutans.*" *Caries Res* 25:116.

Hirose H, Hirose K, Isogai E, Miura H and Ueda I. 1993. "Close Association between *Streptococcus sobrinus* in the Saliva of Young Children and Smooth-Surface Caries Increment." *Caries Res* 27: 292.

Tavares D, Ferreira P, and Arala-Chaves M. 200. "Increased resistance to Systemic Candidiasis in Athymic or Interleukin-10-Depleted Mice." *J Infec. Dis* 182: 266.

Vilanova M, Ferreira P, Ribeiro A, Arala-Chaves M. 1999. "The biological effects induced by p36, a proteinaceous factor of virulence produced by African swine fever virus, are mediated by interleukin-4 and also to a lesser extent by interleukin-10." *Immunology* 96: 389.

Santarém MMG, Porto MT, Ferreira P, Soares R and Arala-Chaves M. 1987. "Semipurification of an Immunosuppressor Substance Secreted by *Streptococcus mutans* that Plays a Role in the Protection of the Bactéria in the Host." *Scand J Immunol* 26 : 755.

Veiga-Malta I, Duarte M, Dinis M, Tavares D, Videira A and Ferreira P. 2004. "Enolase from *Streptococcus sobrinus* is an Immunosuppressive protein." *Cellular Microbiology* 6: 79.

Ferreira P, Brás A, Tavares D, Vilanova M, Ribeiro A, Videira A and Arala-Chaves M. 1997. "Purification, and biochemical and biologic characterization of an immunosuppressive and lymphocyte mitogenic protein secreted by *Streptococcus sobrinus.*" *Int Immunol* 9: 1735.

Lowry Oh, Rosebrough NJ, Farr AL and Randall RJ. 1951. "Protein Measurement with the Folin Phenol Reagent." *J BIol Chem* 193:265.

Keyes PH. 1958. "Dental Caries in the Molar Teeth of Rats. II. A Method for Diagnosing and Scoring Several Types of Lesions Simultaneously." *J Dent Res* 37:1088.

Smith, G.E., "Tooth Decay in the Developing World: Could a Vaccine Help Prevent Cavities?" *Presp Biol Med* 31:331, 1988.

* cited by examiner

A

B

C

# VACCINE AGAINST DENTAL CARIES BASED ON VIRULENCE-ASSOCIATED IMMUNOMODULATORY EXTRACELLULAR PROTEINS PRODUCED BY THE CARIOGENIC BACTERIA *STREPTOCOCCUS SOBRINUS* AND *STREPTOCOCCUS MUTANS*

FIELD OF THE INVENTION

Dental caries is considered one of the commonest infectious diseases affecting man. The development of a vaccine against dental decay has been exhaustively researched for several years. *Streptococcus sobrinus* and *Streptococcus mutans* are the main etiologic agents of dental caries in mammals, man inclusive. The said bacteria excrete into the culture medium virulence-associated immunomodulatory extracellular proteins (VIP), which have a mitogenic effect on the lymphocytes, suppress the immune response of the host and induce in the latter an early production of IL-10, an immunosuppressor cytokine. So, these VIP are important virulent factors to the produced microorganisms and closely associated with the respective bacterial pathogenicity. In this invention, we shall use these proteins as target antigens in a vaccine against dental caries resorting to the immunoneutralization of their immunobiological effects by immunization with submitogenic doses or by the inactivated VIP.

BACKGROUND OF THE INVENTION

The classical strategy in human vaccination based on the immunostimulation of the microorganism structural antigens has been somewhat disappointing. The number of authorized vaccines used to confer immunity in humans represents a very small percentage of all the pathogenic microorganisms known worldwide. There is not yet available any effective vaccine against fungi, protozoa or helminths. However, several findings suggest that vaccination proves to be efficacious when immunoneutralization of microbial agents associated with virulence occurs. Two of the most effective human vaccines, tetanus and diphtheria, are directed towards bacterial toxins and not to the bacteria structural epitopes. It is also worth mentioning that the vaccine against smallpox consists of a virus, not completely attenuated, since vesicles and pustules appear on the skin at the vaccination site. In previous studies, the inventors of the vaccine against dental caries have demonstrated that several pathogenic microorganisms release virulence-associated immunomodulatory proteins (1-.4). The immunoneutralization of these proteins developed a preventive action in the host, protecting it against systemic infections caused both by the fungus *Candida albicans* and the bacterium *Streptococcus mutans* (5,6). Furthermore, preventive vaccination against systemic candidiasis occurred for the first time in primates (marmosets) through immunization against the immunomodulatory protein produced by the fungus (D. Tavares, unpublished communication). Recently, it was reported that a racemase excreted by the protozoon *Trypanosoma cruzi* (7) preventively protects the host from the systemic infection caused by the parasite (Patent application PCT/IB00/02008, from the Pasteur Institute et al., submitted on Dec. 4, 2000).

The bacteria *Streptococcus sobrinus* and *S. mutans* have already been identified as the main etiologic agents of tooth decay in humans (8-11). The treatment of dental caries probably is the most expensive one at world level due to the disease high incidence all over (8,11). Both children and teenagers as well as adults can benefit from vaccination since it prevents pathological complications associated with cariogenicity. Actually, it is well known that Streptococci infections are responsible, in 55% of the cases, for endocarditis and are frequently detected in immunodepressed patients. Therefore, a vaccine against dental decay will reduce risk factors in patients suffering from congenital heart disease or having a heart implanted device and will have a helpful effect on other pathologies or clinical disorders associated with bacterial colonization.

The cariogenic bacteria *S. sobrinus* and *S. mutans* excrete into the culture medium proteins whose characteristics are identical to those reported in other microorganisms (1-4). These proteins have in common the following: i) they are mitogenic proteins, inducing lymphocyte polyclonal activation in the host (1-4); ii) they induce the early production of IL-10, an anti-inflammatory cytokine (12,13); iii) they are associated with the microorganism virulence once there is a direct relationship between its production and the microbe pathogenicity (4,14) and are iv) important to the survival of the microorganism in the host as the treatment of the latter with these proteins before occurring the infection enhances the parasitic loading (2,4,14). Consequently, the production of these immunomodulatory proteins seems to be an evasion mechanism used by some pathogens. The protein responsible for the immunosuppressor activity of the VIP produced by *S. sobrinus* was recently identified as an enolase according to a N-terminal basis and the gene that encodes it cloned, sequenced and expressed into a heterologous system in order to obtain the recombinant protein (15).

SUMMARY OF THE INVENTION

This invention uses virulence-associated immunomodulatory extracellular proteins (VIP). Though the vaccination strategy is identical to the one described for the already mentioned microbes, there are some innovative differences that deserve special reference:
  I) the etiologic agents are the bacteria *S. sobrinus* and *S. mutans*;
  II) dental caries is the infection caused by these bacteria;
  III) tooth infection occurs via oral;
  IV) vaccination routes are: oral, intranasal and subcutaneous;
  V) this vaccination has two main objectives: prevention and infection treatment when it occurs.

BRIEF DESCRIPTION OF THE DRAWINGS

FIG. 1 shows results of 1 of 3 representative independent experiments.

DETAILED DESCRIPTION OF THE INVENTION

Figure 1:
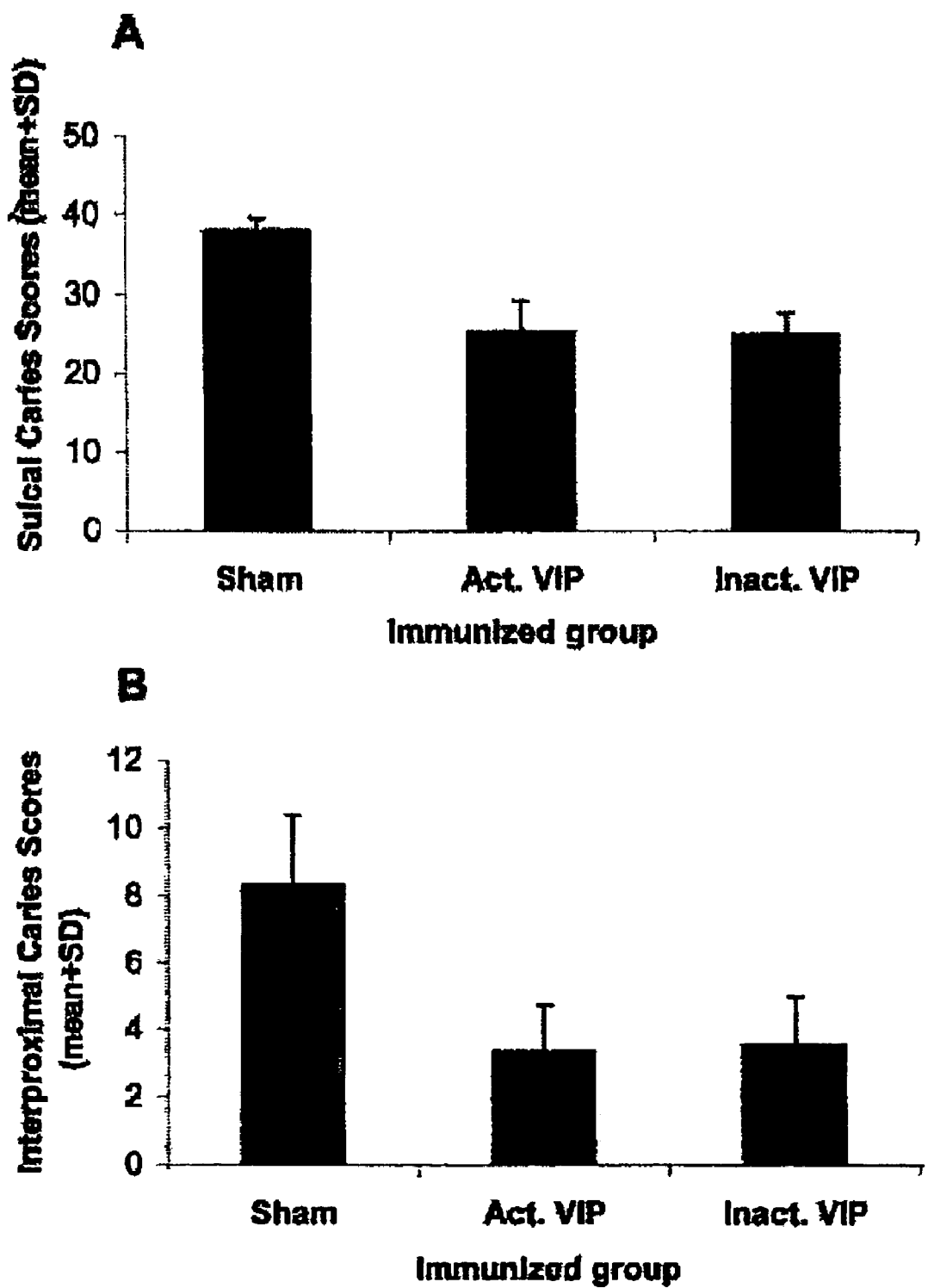
FIG. 1 shows evaluation of dental caries scores on proximal (A) and sulcal (B) molar surfaces involving enamel lesions in Wistar rats sham-immunized and active- or heat-inactivated-VIP-immunized. Data show means±SD of 10 to 12 rats per group. Statistical difference in mean score among the 3 groups was assessed by ANOVA. Multiple comparisons among groups indicated a significantly different mean score of active- or inactive-VIP-immunized in comparison with sham-immunized (p<0.001). No differences were detected between active- and heat-inactivated-VIP-immunized groups.

This invention aims at marketing a vaccine against dental decay, obtained from the supernatant over cultures of the cariogenic bacteria known as *Streptococcus sobrinus* and *S. mutans*.

According to this invention, the vaccine consists of extracellular proteins or recombinant enolase.

The said proteins induce the suppression of the immune response in the host through the early production of IL-10, an anti-inflammatory cytokine.

In addition, those proteins are factors of virulence to the host and enhance the respective bacterial colonization.

This vaccine induces the immunoneutralization of the immunobiological effects caused by virulence-associated immunomodulatory extracellular proteins (VIP) through the host immunization with submitogenic doses of VIP or inactivated VIP.

Further to this invention, the vaccine against dental decay is prepared to be administered intranasally, orally or subcutaneously to mammals.

This vaccine may be used as a preventive measure against dental caries, i.e., immunization with VIP is performed before bacterial infection.

Alternatively, this vaccine may be administered as an effective treatment of dental caries by immunization with VIP after bacterial infection

EXPERIMENTAL PART

Preparation Procedure

Preparation of Virulence-Associated Immumodulatory Extracellular Proteins (VIP)

I) Preparation of the Set of Extracellular Proteins from the Bacteria *S. sobrinus* and *S. mutants*

The bacteria were cultured anaerobically in a broth medium of Todd-Hewitt for 2 days at 37° C. in a starting concentration of $10^8$ microorganisms/ml as previously reported (14,16). Cultures were centrifuged at 29,000×g during 30 mm and the supernatants successively filtered using 1.2 µm, 0.45 µm and 0.2 µm filters (Schleicher & Schuell). The supernatants were then concentrated by ultracentrifugation (dialysis membrane of 10 kDa porosity) in a Vivaflow 200 (Masterflex, easy-load) system. These products were generically designated as crude extracellular proteins of their respective bacteria (CEP-Ss and CEP-Sm).

II) CEPs Fractionation

CEPs were subject to an ion-exchange chromatography as previously described (16). The different fractions were concentrated by means of vacuum dialysis on membranes of 12 kDa porosity. Protein concentration was determined according to the Lowry's method (17). Fractions with biological activity (described below) were subfractionated by isoelectric focusing in 2.5-10 saccharose gradient, using an ampholyte mixture of pH 2.5-5.0 and 4.5-6.0 (Pharmacia) as already reported (16). The eluted fractions with biological activity and a pH 4.0-5.0 were designated as protein fractions with virulence-associated immunomodulatory activity, VIP in short.

III) Isolation and Purification of Recombinant Enolase

Cultures of *Escherichia coli* M-15 cells under exponential growth ($A_{600}$=0.6-0.8) and expression vector pQE-31 were induced into the fusion protein expression during 3 hrs at 37° C. by adding 1 mM IPTG (15). The cells were collected by centrifugation at 5000×g for 20 min and resuspended in phosphate buffer (1 mM $Na_2HPO_4.2H_2O$, 1 mM $NaH_2PO_4.H_2O$, 50 mM NaCl, pH 7.4) containing 10 mM imidazole. The sample was incubated on ice during 30 min in the presence of 100 µg/ml lysozyme and 1% Triton X-100. The cells were sonicated at maximum intensity in 3 cycles of 10 sec. The insoluble material was removed by centrifugation at 10000×g for 15 min. The supernatant was filtered using filters of 0.45 µm porosity and introduced into a His-trap column. The recombinant enolase was eluted by imidazole under native conditions. Protein concentration was measured by the Lowry's method (17). The purity of the recombinant protein was determined by SDS-PAGE on gel at 17.5%.

APPLICATION EXAMPLES

Animal models: C57BL/6 mice aged 8-10 weeks born at the Gulbenkian Institute for Science, Oeiras, were used in immunobiological assays. Male and female 16-day old Wistar rats born at the animal quarters of the Faculty of Medicine in Coimbra were used in dental caries experiments. The rats were weaned when they were 20 days old and started a cariogenic diet on the $16^{th}$ day following birth.

Bacteria: *Streptococcus sobrinus*, strain 6715, obtained from the "American Type Culture Collection (ATCC, Manassas, Va.) and *Streptococcus mutans* (kind gift of Institute Pasteur, Paris), stored at −70° C. in a culture medium of "Brain Heart Infusion Broth" (Difco, Detroit, Mich.) with 25% (v/v) glycerol.

Example A1

Evaluation of the Immunobiological Activity of VIP and of the Protein Recombinant Enolase of *S. sobrinus*

As it has been previously described (16), the polyclonal activation induced by VIP was determined 5 days after the VIP mice inoculation by the number of non-specific immunoglobulin producing spleen cells, the IgM and IgG isotypes. The isotype profile obtained was IgG2a>IgG2b>IgG1>−IgG3>IgM. The analysis of cell activation markers of the splenic lymphocyte total population 6 hrs (CD69) and on days 3 and 5 (CD25) after treatment with VIP showed a preferential increase in the expression of both markers in the population of B lymphocytes. The immunosuppressor effect was determined following injection of VIP or recombinant enolase 4 days before intraperitoneal immunization with sheep red blood cells (SRBC), as previously reported (15,16,). It was observed an evident suppression of the specific response against SRBC in comparison with the controls. It was also detected that this VIP and the recombinant enolase induced in the inoculated mice a fast increase in the serum levels of interleukin-10 (IL-10) with the maximum rise observed 2 hrs after i.p. injection.

Example A2

Experimental Immunoprotection Assay Using the VIP from *Streptococcus sobrinus* and Recombinant Enolase.

Protocol for Dental Caries Experiments with Wistar Rats

I) Antigens and adjuvant. The VIP of *Streptococcus sobrinus* was used as active VIP in a submitogenic dose or inactivated VIP and the recombinant enolase was used in a dose unable to induce immunosuppression. Alum, a kind gift of Erik Lindblad (Biosector, Denmark), was used as adjuvant.

II) Immunizations. Male and female Wistar rats were used in these experiments. Groups of 10-12 animals each were subject to the following treatment:

We conducted these experiments to investigate the protective effect of therapeutic immunization with the active- or inactivated-VIP or with recombinant enolase in *S. sobrinus*-induced dental caries in Wistar rats.

The differences in enamel sulcal caries score between sham-immunized group and the other two immunized groups were statistically significant (p<0.001), with a 34% reduction in caries lesions in both immunized groups of rats (FIG. 1A). The protective effect of VIP immunization on caries lesions was more marked in the enamel proximal caries score (FIG. 1B). Indeed, the differences in the proximal caries scores between the sham-immunized group and the two VIP-immunized groups were statistically relevant (p<0.001), with a 60% reduction in the caries lesions in both VIP-immunized

|  | Group I (Sham.-immunized or control) | Group II (immunized intranasally with active VIP) | Group III (immunized intranasally with inactivated VIP) | Group IV (immunized orally with Recombinant enolase) |
|---|---|---|---|---|
| 16$^{th}$ day 17$^{th}$-21$^{st}$ day | Cariogenic diet Colonization of the oral cavity with 10$^9$ cells of *S. sobrinus* | Cariogenic diet Colonization of the oral cavity with 10$^9$ cells of *S. sobrinus* | Cariogenic diet Colonization of the oral cavity with 10$^9$ cells of *S. sobrinus* | Cariogenic diet Colonization of the oral cavity with 10$^9$ cells of *S. sobrinus* |
| 4 days later | 1$^{st}$ intranasal (i.n.) or oral immunization with PBS + Alum | 1$^{st}$ i.n. immunization with active VIP + alum | 1$^{st}$ i.n. immunization with inactivated VIP + alum | 1$^{st}$ oral immunization with recombinant enolase + alum |
| 3 weeks later | 2$^{nd}$ i.n. or oral. immunization with PBS + Alum | 2$^{nd}$ i.n. immunization with active VIP + alum | 2$^{nd}$ i.n. immunization with inactivated VIP + alum | 2$^{nd}$ oral immunization with recombinant Enolase + alum |
| 10 weeks later | The animals were sacrificed and dental caries evaluated | The animals were sacrificed and dental caries evaluated | The animals were sacrificed and dental caries evaluated | The animals were sacrificed and dental caries evaluated |

Evaluation of Dental Caries in the Experimental Groups

The rats of the different groups were sacrificed when they were 120 days old and identified with codified numbers before being sent to another laboratory to evaluate dental caries incidence and severity. The jaws were removed and sectioned longitudinally, stained with silver nitrate at 5% for 72 hrs and cut sagittally. The extent of enamel or dentine caries lesions in the 1$^{st}$, 2$^{nd}$ and 3$^{rd}$ molars teeth of all rats (caries score) was microscopically evaluated by a modified method of Keyes (18).

Bacterial Recoveries

*S. sobrinus* infection levels were assessed after systematic swabbing of teeth, sonication, and plating of appropriate dilutions on Todd-Hewitt agar (Difco) with Strreptococcus Selective Supplement (0.001 mg of colistin sulphate and 0.5 μg of oxalinic acid per ml) (Oxoid). The plates were incubated at 37° C. in aerobiose for 48 hrs, and *S. sobrinus* CFU were then enumerated microscopically.

Statistical Analysis

The level of significance of the results in all groups of rats was determined by one-way ANOVA, calculated with Microsoft Excel 2000 software.

Example A3

Increased Resistance to *Streptococcus sobrinus*-Induced Dental Caries in Rats by Intranasal or Oral Therapeutic Vaccination with the VIP or with Recombinant Enolase, Respectively.

groups (FIG. 1B). No statistical differences were found between active- and inactivated-VIP-immunized groups (p=1.000). Therefore, immunization with either active or inactivated VIP conferred protection against *S. sobrinus*-induced dental caries in Wistar rats.

The evaluation of *S. sobrinus* colonization in the oral cavities of the rats showed that VIP-immunized groups exhibited a significant reduction in *S. sobrinus* levels, while the sham-immunized group maintained high levels of bacteria throughout the study.

TABLE

Reduction of *S. sobrinus* Oral Colonization in Acive- or Heat-inactivated-VIP-immunized Rats[a]

| | Mean Response (log CFU ± log SD[b]) | | |
|---|---|---|---|
| Days after Immunization | Sham-immunized | Active-VIP-immunized | Heat-inactivated-VIP-immunized |
| 30 | 7.62 ± 0.66 | 6.76 ± 0.65 | 6.62 ± 0.54 |
| 60 | 6.60 ± 0.56 | 5.43 ± 0.58 | 5.61 ± 0.68 |
| 90 | 5.89 ± 0.74 | 4.23 ± 0.60 | 4.27 ± 0.61 |

[a]Numbers of *S. sobrinus* CFU recovered from the oral cavities of the different groups of Wistar rats orally infected with *S. sobrinus* 4 days before immunization (post-infection immunization).
[b]Results are means ± SD of 10 to 12 Wistar rats per group. The significantly higher differences between sham-immunized and active- or heat-inactivated-VIP-immunized groups are underlined (p < 0.001).
Statistical difference in mean score among the 3 groups was assessed by ANOVA.

Figure 2:
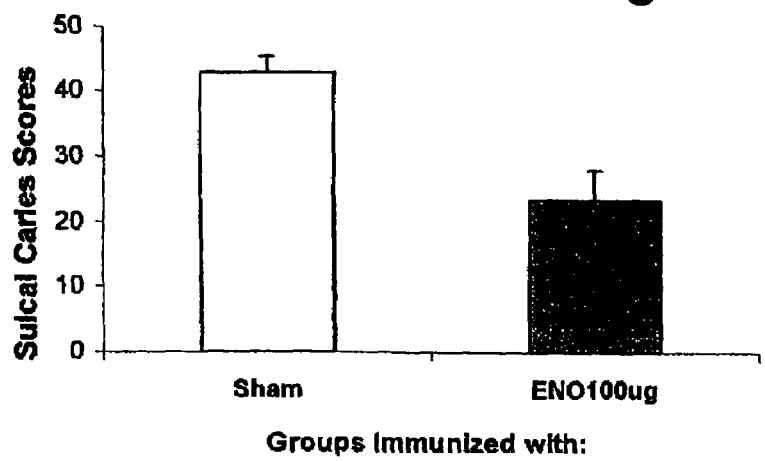
FIG. 2 shows caries lesions on sulcal (A) and interproximal (B) enamel and dentine (C) of molar surfaces in sham-immunized and ENO-immunized rats. Values are the mean caries scores±the standard deviations of 10 to 12 Wistar rats and are one of three representative independent experiments. Comparison among groups indicated a significant difference between ENO-immunized and sham-immunized animals (p<0.001).
Figure 2:
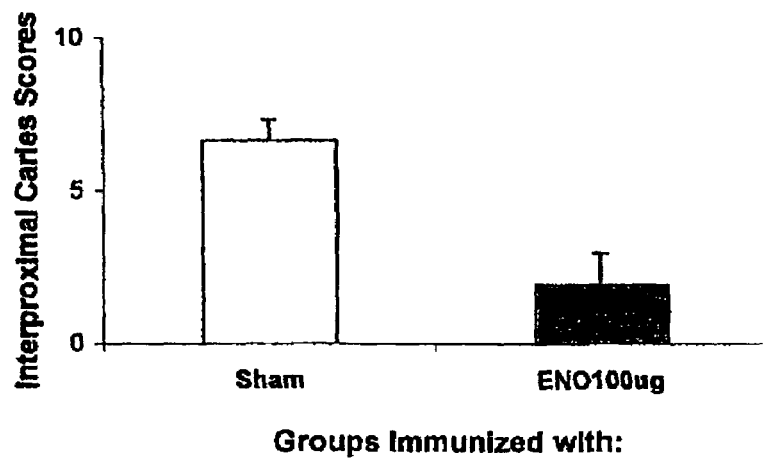
Figure 2:
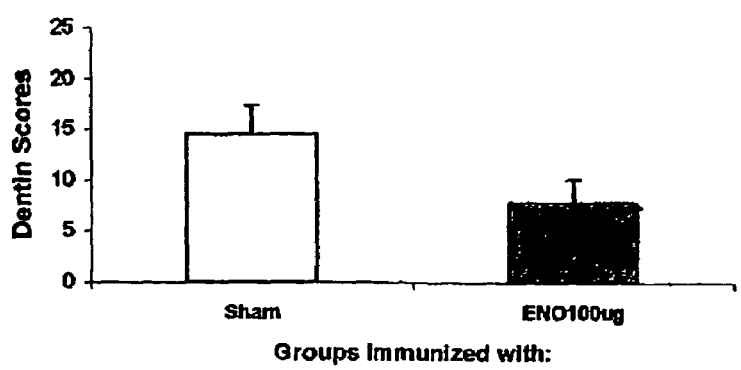

The evaluation of dental caries in the animal group orally immunized with recombinant enolase showed that cariogenic lesions in these rats were significantly lower either on the enamel or dentine in comparison with the controls (p<0.001). Therefore, as shown in FIG. 2A there was a reduction of 45% reduction in the enamel sulcal caries score on ENO-immunized group comparatively with sham-immunized animals. This protective effect of enolase immunization on teeth lesions was more evident in the enamel interproximal caries score (FIG. 2B). Indeed, a 71% reduction was observed in the interproximal caries lesions on the ENO-immunized group when compared with the sham-immunized. Moreover, a reduction of 46% in the dentine lesions on the ENO-immunized group was observed when compared with sham-immunized animals (FIG. 2C).

Figure 3:
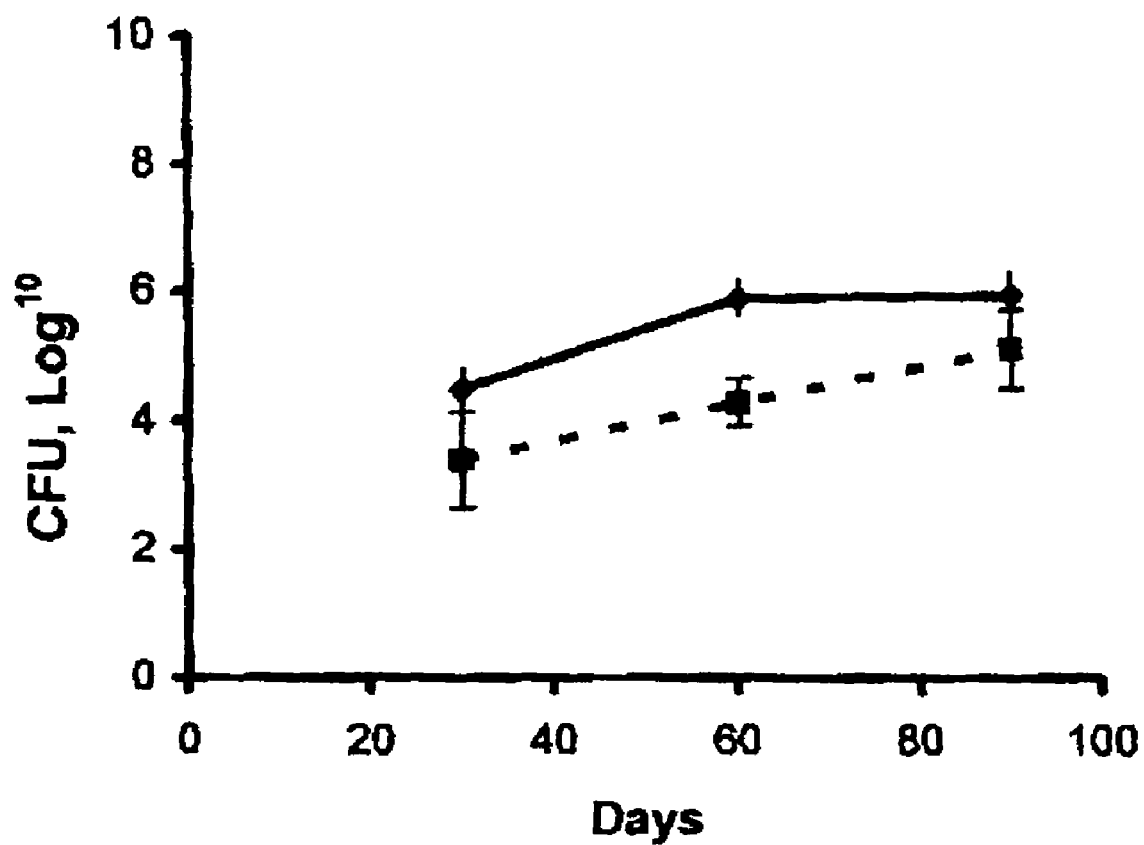
FIG. 3 shows numbers of *S. sobrinus* CFU (Log 10) recovered from oral cavities of different groups of Wistar rats orally infected with *S. sobrinus* 4 days before immunization. Results are the means±SD of 10 to 12 rats per group rats and are one of three representative independent experiments. Comparison among groups indicated a significant difference between ENO-immunized (...) and sham-immunized (—) animals (p<0.001).

The evaluation of *S. sobrinus* colonization in the rats oral cavity showed a significant reduction in *S. sobrinus* levels on ENO-immunized rats when compared with the sham-immunized group, throughout the study (FIG. 3). This reduction of *S. sobrinus* colonization in oral cavity of ENO-immunized group, in comparison with sham-immunized animals, is correlated with the reduction of caries lesions observed in ENO-immunized rats.

The greater resistance against dental caries observed in the animals immunized against VIP or against the recombinant enolase is in agreement with the important role played by these proteins as to colonization enhancement brought about by the producing bacteria.

BIBLIOGRAPHY

1. Arala-Chaves M P, Ribeiro A, Vilanova M, Porto M T, Santarém, M M G and Lima M. 1988. Correlation between B cell mitogenicity and immunosuppressor effects of a protein released by porcine monocyte infected with African swine fever virus. *Am J Vet Res* 49:1955.
2. Lima M, Bandeira A, Portnoi D, Ribeiro A, Arala-Chaves M P. 1992. Protective effect of a T-cell-dependent, immunosuppressive, B-cell-mitogenic protein (F3'EP-Si or p90) produced by *Streptococcus intermedius*. *Infect Immun* 60: 3571.
3. Ferreira P, Soares R, Ribeiro A, and Arala-Chaves M. 1988. Correlation between specific immunosuppression and polyclonal B cell activation induced by a protein secreted by *Streptococcus mutans*. *Scand J Immunol* 27: 549.
4. Tavares D, Salvador A, Ferreira P, and Arala-Chaves M. 1993. Immunological activities of a *Candida albicans* protein which plays an important role in the survival of the microorganism in the host. *Infect Immun* 61: 1881.
5. Tavares D, Ferreira P, Vilanova M, Videira A and Arala-Chaves M. 1995. Immunoprotection against systemic candidiasis in mice. *Int Immunol* 7:785.
6. Soares R, Ferreira P, Santarém M M G, Teixeira da Silva M, and Arala-Chaves, M. 1990. Low T- and B-cell reactivity is an apparently paradoxical request for murine immunoprotection against *Streptococcus mutans*. *Scand J. Immunol* 31:361.
7. Reina-San-Martin B, Degrave W, Rougeot C, Cosson A, Chamond N, Cordeiro-Da-Silva A, Arala-Chaves M, Coutinho A and Minoprio Paola. A B-cell mitogen from a pathogenic trypanosome is a eukaryotic proline racemase. *Nature Medicine* 6: 890.
8. Loesche, W J. 1996. Role of *Streptococcus mutans* in human dental decay. Microbiol Rev 50:353.
9. De Soet J J, van Leveren C. Lammens A J, Pavicic M J A, Homburg C H E, Cate J M and Graaff J. 1991. Differences in cariogenicity between fresh isolates of *Streptococcus sobrinus* and *Streptococcus mutans*. *Caries Res* 25:116.
10. Hirose H, Hirose K, Isogai E, Miura H and Ueda I. 1993. Close association between *Streptococcus sobrinus* in the saliva of young children and smooth-surface caries increment. *Caries Res* 27: 292.
11. Smith G E. 1988. Tooth decay in the developing world: could a vaccine help prevent caries? *Presp Biol Med* 31:331.
12. Tavares D, Ferreira P, and Arala-Chaves M. 2000. Increased resistance to systemic candidiasis in athymic or interleukin-10-depleted mice. *J. Infect. Dis* 182: 266.
13. Vilanova M, Ferreira P, Ribeiro A, Arala-Chaves M. 1999. The biological effects induced by p36, a proteinaceous factor of virulence produced by African swine fever virus, are mediated by interleukin-4 and also to a lesser extent by interleukin-10. *Immunology* 96: 389.
14. Santarém M M G, Porto M T, Ferreira P, Soares R and Arala-Chaves M. 1987. Semipurification of an immunosuppressor substance secreted by *Streptococcus mutans* that plays a role in the protection of the bacteria in the host. *Scand J Immunol* 26: 755.
15. Veiga-Malta I, Duarte M, Dinis M, Tavares D, Videira A and Ferreira P. 2004. Enolase from *Streptococcus sobrinus* is an immunosuppressive protein. *Cellular Microbiology* 6: 79.
16. Ferreira P, Brás A, Tavares D, Vilanova M, Ribeiro A, Videira A and Arala-Chaves M. 1997. Purification, and biochemical and biologic characterization of an immunosuppressive and lymphocyte mitogenic protein secreted by *Streptococcus sobrinus*. *Int Immunol* 9: 1735.
17. Lowry O H, Rosebrough N J, Farr A L and Randall R J. 1951. Protein measurement with the Folin phenol reagent. *J Biol Chem* 193:265.
18. Keyes P H. 1958. Dental caries in the molar teeth of rats. II A method for diagnosing and scoring several types of lesions simultaneously. *J Dent Res* 37:1088.

The invention claimed is:

1. A method for vaccination of a mammal against dental caries, which comprises the administration intranasally, orally or subcutaneously of a therapeutically-effective amount of a vaccine comprising a virulence-associated immunomodulatory extracellular protein from the bacteria *Streptococcus sobrinus* or *Streptococcus mutans* or a recombinant enolase to said mammal, wherein the vaccine will act through the immunoneutralization of the immunobiological effects of the virulence-associated immunomodulatory extracellular proteins (VIP) after host immunization with submitogenic doses of inactivated VIP or with enolase in a dose unable to induce immunosuppression.

2. The method of claim 1, wherein the vaccine is administered to humans.

3. The method of claim 1, wherein said vaccine against dental caries is administered as a preventive measure against this tooth disease by means of VIP or enolase immunization performed before bacterial infection.

4. The method of claim 2, wherein said vaccine against dental caries is administered as a preventive measure against this tooth disease by means of VIP or enolase immunization performed before bacterial infection.

5. A method of preventively vaccinating a mammal against dental caries, comprising the step of intranasally, orally or subcutaneously administering a therapeutically-effective amount of a vaccine comprising a virulence-associated immunomodulatory extracellular protein (VIP) from the bacteria *Streptococcus sobrinus* or *Streptococcus mutans* or a recombinant enolase to said mammal.

6. The method of claim 5, wherein the vaccine includes at least one protein selected from the group consisting of:
   a. a VIP of *Streptococcus sobrinus* selected from the group consisting of: an active VIP and an inactivated VIP; and
   b. a recombinant enolase in a dose that does not induce immunosuppression.

7. The method of claim 5, wherein the vaccine comprises:
   a. an active VIP of *Streptococcus sobrinus* or *Streptococcus mutans* in a submitogenic dose;
   b. an inactivated VIP of *Streptococcus sobrinus* or *Streptococcus mutans* in a dose that does not induce immunosuppression; or
   c. a recombinant enolase in a dose that does not induce immunosuppression.

8. The method of claim 5, wherein the vaccine is administered orally.

9. The method of claim 5, wherein the vaccine further comprises an adjuvant.

10. A method of preventively inducing resistance to dental carries comprising the step of administering to a human, the method comprising the step of administering intranasally, orally or subcutaneously a therapeutically effective dose of a vaccine including at least one of the following:
    a. an active virulence-associated immunomodulatory extracellular protein (VIP) of *Streptococcus sobrinus* or *Streptococcus mutans* in a submitogenic dose;
    b. an inactivated VIP of *Streptococcus sobrinus* or *Streptococcus mutans* in a dose that does not induce immunosuppression; and
    c. a recombinant enolase in a dose that does not induce immunosuppression.

11. The method of claim 1, wherein the vaccine is administered intranasally or orally.

12. The method of claim 5, wherein the vaccine is administered intranasally or orally.

13. The method of claim 10, wherein the vaccine is administered intranasally or orally.

14. The method of claim 1 wherein the vaccine comprises the virulence-associated immunomodulatory extracellular proteins (VIP), the VIPs having a molecular weight between 30-50 kDa and pH between 3.0 and 5.0.

15. The method of claim 1 wherein the vaccine comprises the enolase, the enolase having a molecular weight of 47 kDa and pH 4.75.

16. The method of claim 1 wherein the vaccine comprises the enolase, wherein the therapeutically-effective amount of enolase is at least 100 µg.

17. The method of claim 1 wherein the vaccine is effective at at least one of thirty days, sixty days, or ninety days after immunization.

18. The method of claim 1 wherein the vaccine comprises the enolase, wherein the enolase has the ability to induce suppression of the immune response in a host through the production of IL-10, an anti-inflammatory cytokine.

19. The method of claim 1 wherein the vaccine comprises the enolase, wherein the enolase is obtained by gene cloning and sequencing of *S. sobrinus* enolase, expressed in a heterologous system viewing the obtention of the recombinant protein.

20. The method of claim 1 wherein the vaccine comprises a virulence-associated immunomodulatory extracellular protein from the bacteria *Streptococcus sobrinus* or *Streptococcus mutans*, wherein the protein has the ability to induce suppression of the immune response in a host through the production of IL-10, an anti-inflammatory cytokine.

* * * * *